United States Patent [19]

Yamazaki et al.

[11] Patent Number: 4,613,359
[45] Date of Patent: Sep. 23, 1986

[54] FLOWER-THINNING AGENT FOR FRUIT TREES

[75] Inventors: Toshihiko Yamazaki; Shoji Murase, both of Sakura; Katsuyuki Suzuki, Tsuchiura; Makoto Iwatsuki, Yokosuka, all of Japan

[73] Assignees: Director, Fruit Tree Research Foundation; Ajinomoto Co., Ltd., both of Tokyo, Japan

[21] Appl. No.: 473,354

[22] Filed: Mar. 8, 1983

[30] Foreign Application Priority Data

Mar. 12, 1982 [JP] Japan .................................. 57-37976

[51] Int. Cl.$^4$ .......................................... A01N 31/00
[52] U.S. Cl. ......................................... 71/122; 71/88; 71/95; 71/118
[58] Field of Search ....................... 71/122, 70, 74, 75, 71/88, 95, 118

[56] References Cited

U.S. PATENT DOCUMENTS 3,971,651 7/1976 Hashimoto et al. .................. 71/122

OTHER PUBLICATIONS

Kopcewicz, Chem. Abst., vol. 71 (1969) 19598p.
Chakraborty et al., Chem. Abst., vol. 83, (1975) 160933y.
Biswas et al., Chem. Abst., vol. 66 (1967) 84941f.

Primary Examiner—Catherine L. Mills
Attorney, Agent, or Firm—Larson and Taylor

[57] ABSTRACT

A new flower-thinning agent is now provided, which is comprising as the active component 2-pyrrolidone-5-carboxylic acid, a salt thereof, a salt of an N-higher aliphatic acyl acidic amino acid, an ester of sugar with a higher fatty acid, or a plant sterol and advantageously exerts the flower-thinning effects superior to the known flower-thinning agents.

2 Claims, 3 Drawing Figures

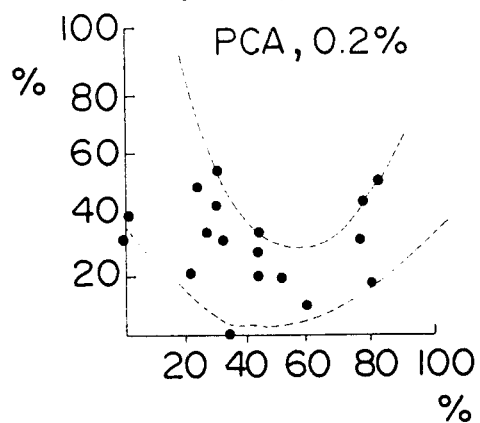
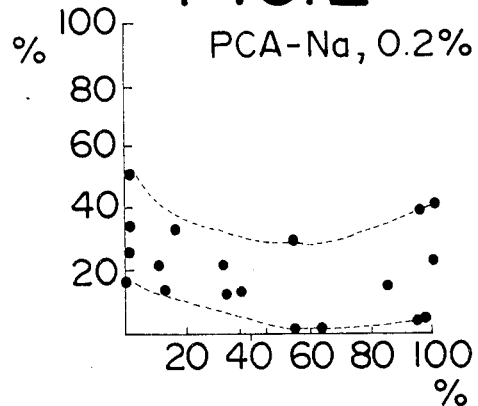
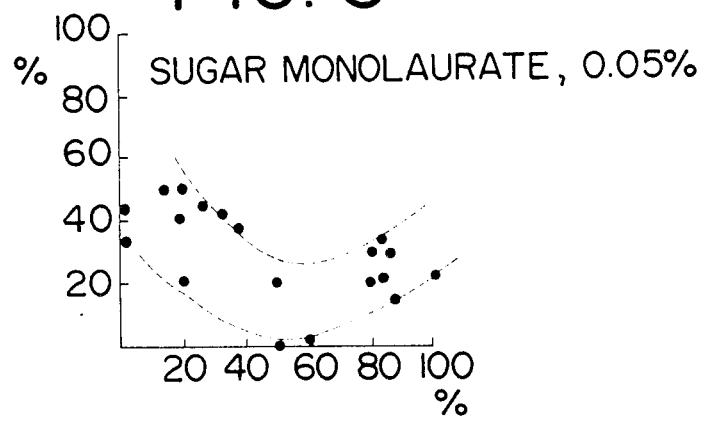

FLOWER-THINNING AGENT FOR FRUIT TREES

SUMMARY OF THE INVENTION

This invention relates to a new flower-thinning agent for use in thinning treatment of flowers of fruit trees of various kinds. More particularly, this invention relates to a new flower-thinning agent which is applied to flowers of fruit trees cultivated, for the purpose of partially removing or thinning the such flowers which are not required to undergo the fructification, with retaining on the tree such flowers which are required to fructify.

BACKGROUND OF THE INVENTION

In the cultivation of fruit trees of various kinds, it is essential to make preliminary works for picking off some bodies of flower or fruit which are not required to fructify. Such works for picking off the unrequired bodies of flower or fruit are known as "thinning" of flower or fruit. Meanwhile, such thinning of flower or fruit usually needs a large amount of labor by the workers. The thinning works usually must be done in such seasons of busy work in agriculture, and hence it is frequently difficult to make the thinning works at an appropriate time therefor, so that the quality of the fruits cultivated and harvested could be lowered sometimes.

Heretofore, the methods for thinning the flower or fruit of fruit trees by chemical compounds have been extensively researched for almost all kinds of fruit trees such as apple tree, peach tree and others, and there have been proposed and developed a number of chemical thinning agents. The known chemical thinning agents may be classified according to their biological mechanisms of the action of these agents, and they may largely be classified into two groups, that is, a first group of such agents which act as a plant hormone and the second group of such agents which can exert a phytotoxicity against the bodies or different organs of flower of the fruit trees. While, such chemical thinning agents which have been extensively applied in practice for partial removal of the unrequired flowers or fruits are limited only to the formulation known as the name "Ethyclozate" for use in the thinning treatment of tangerine tree; the formulation known as the name "Sevin" for use in the thinning treatment of apple tree; and certain sulfur preparations for use in the thinning treatment of apple tree. The active components of the thinning agents known under the names "Ethyclozate" and "Sevin" are belonging to a class of plant hormone in nature, so that their flower-thinning effects can unfavorably vary depending on the biological conditions of the trees treated and also on the weathering conditions, which is specifically observed with the plant hormone agents in usual. On the other hand, the sulfur preparations practically employed as the chemical thinning agent are active to inhibit the fertilization of flowers owing to its phytotoxicity to the stigma of the flower body, so that its flower-thinning activity is normally lower than those of the flower-thinning agents of plant hormone type. When the sulfur preparations are applied in an increased rate of application in an attempt to enhance its flower-thinning effects, the leaves and other portions of the fruit tree as treated can often be damaged by the phytotoxicity of the sulfur preparations.

For these reasons, there exists a great demand for a new flower-thinning chemical agent which is free from the above-mentioned drawbacks of the known chemical flower-thinning agents. In an attempt to meet this demand, we have researched a number of chemical compounds which are different in nature from the active components of the known thinning agents, and we have now found that 2-pyrrolidone-5-carboxylic acid and salt thereof such as the sodium salt; and salt of an N-higher aliphatic acylated acidic amino acid; as well as an ester of sugar with a higher fatty acid and plant sterols are each active to thin the flowers of the cultivated fruit trees.

DETAILED DESCRIPTION OF THE INVENTION

According to an embodiment of this invention, therefore, there is provided a new flower-thinning agent comprising as the active component an effective amount of at least one of 2-pyrrolidone-5-carboxylic acid, a salt thereof, a salt of an N-higher aliphatic acylated acidic amino acid, an ester of sugar with a higher fatty acid, and plant sterols, in association with a suitable carrier for the active component.

According to a further embodiment of this invention, there is provided a method for thinning flowers of the cultivated fruit trees, which comprises applying to the flowers and/or to the body of the fruit trees an effective amount of at least one of 2-pyrrolidone-5-carboxylic acid, a salt thereof, a salt of an N-higher aliphatic acylated acidic amino acid, an ester of sugar with a higher fatty acid and plant sterols.

This invention also includes applications of the above-mentioned active component compounds as a flower-thinning agent.

The active component of the flower-thinning agent according to this invention may be, in addition to free 2-pyrrolidone-5carboxylic acid, a salt thereof, for example, an alkali metal salt such as sodium salt, an ammonium salt thereof, a salt thereof with an organic amine such as methylamine, ethylamine, triethylamine, monoethanolamine, diethanolamine, triethanolamine and the like, as well as a salt thereof with a basic amino acid such as ornithine, lysine and the like.

The salt of N-higher aliphatic acylated acidic amino acid used as the active component in this invention may be, for example, a salt of N-higher aliphatic acylated asparatic acid and a salt of N-higher aliphatic acylated glutamic acid. Said N-acyl group may be those derived from saturated or unsaturated fatty acid containing 8 to 22, preferably, 12 to 18 carbon atoms, such as, for example, lauric acid, palmitic acid, stearic acid, oleic acid and the like. The N-acyl group may also be those derived from mixed fatty acids such as, coconut oil fatty acids, tallow fatty acids, hardened tallow fatty acids, and the like. The salt of the N-acylated acidic amino acid may be an alkali metal salt such as sodium or potassium salt, an ammonium salt, a salt with a basic amino acid such as lysine, ornithine and the like, as well as a salt with an organic amine such as triethylamine, monoethanolamine, diethanolamin, triethanolamin and the like.

The higher fatty acid moiety, which is present in ester of said higher fatty acid with sugar may include a saturated or unsaturated fatty acid containing 8 to 22 carbon atoms. Preferably, said esters may be those of sugar with mono-, di- or tri-lauric or myristic acid ester.

The plant sterol may include sitosterol, stigmasterol, campesterol, brassicasterol and the like.

The flower-thinning agent according to this invention is applied to a fruit tree on the flowering time. The flower-thinning agent may be applied to a wide variety of fruit trees such as, for example, pear, peach, persimmon, apple, cherry and so on.

The flower-thinning agent according to this invention may be applied in various form such as a solution, wettable powder, emulsion or spray, by mixing with any suitable solid or liquid carrier such as water. However, it is preferable that the thinning agent is applied in the form of an aqueous solution or dispersion of the active component.

The concentration of the active component in the thinning agent may vary depending on the nature of the fruit tree treated and also on the environmental conditions when the agent is applied, but the concentration is usually of the order of 0.1 to 1.0% by weight, preferably, 0.2 to 0.5% by weight.

The flower-thinning agent according to this invention has the following advantageous characteristics:

(1) The agent of this invention dose not exhibit the flower-thinning effect against such flowers of which the fertilization has been completed, and thus it is possible to select the class of fruit trees from which the flowers are removed by the thinning treatment, if one choose the time when the agent is applied.

(2) The agent of this invention has no phytotoxicity to the plant to which it is applied.

(3) The agent of this invention may effectively be applied to a wide variety of fruit trees.

(4) The agent of this invention has no toxicity against humans and does not cause any environmental pollution.

(5) The agent of this invention is inexpensive.

The following Examples illustrate the invention.

EXAMPLE 1

A solution of 50% (by weight) of 2-pyrrolidone-5-carboxylic acid sodium salt in water was diluted with water to form a sprayable aqueous solution containing the sodium salt at a desired concentration.

EXAMPLE 2

1 Part of monosodium N-mixed fatty acyl glutamate whose the acyl groups were those derived from mixed fatty acids (the composition of the acyl groups: the acyl from semi-hardened tallow fatty acids, plus the acyl from coconut oil fatty acids in a mixed ratio of 8:2) was dissolved in 99 parts of warm water at a temperature of 50° C. to form 100 parts by weight of an emulsion containing the active component at a concentration of 1%.

EXAMPLE 3

An aqueous solution of 40% sucrose mono-laurate was diluted with water to give an aqueous solution containing the sugar mono-laurate at a desired concentration.

EXAMPLE 4

Into 95 parts by weight of dioxane were dissolved 5 parts of a mixture of plant sterols comprising 50% of sitosterol, 28% of campesterol, 15% of stigmasterol and 7% (by weight) of brassicasterol, so that a solution containing 5% of the active sterols was prepared.

The following Examples illustrate the flower-thinning effect of the thinning agent of this invention.

EXAMPLE 5

Flower Thinning of Japanese Pear Tree

The flower-thinning agents of this invention as prepared according to the foregoing Examples 1 to 4 and containing the active component compound at a concentration of 0.01 to 0.5% (by weight) were sprayed onto the flowers of Japanese pear trees (Variety: Housui) before the pollination took place.

At the end of 30 days after the spraying of the agent so prepared, the thinning effects of the agent applied were estimated by counting the number of flower clusters initially tested and the number of all the individual flower bodies initially tested (termed as "number of flowers tested") and by evaluating "percentage of bearing clusters" (which means percentages of the number of the flower clusters of which any individual flower body had been fructified, as calculated on the basis of the total number of the flower clusters which were remaining on the tree even after the thinning treatment); "percentage of fruit set" (which means percentages of the total number of the fructified, individual flower bodies in the flower clusters, as calculated on the basis of the total number of the fructified and unfructified individual flower bodies in the flower clusters which were remaining on the tree even after the thinning treatment); and "average number of fruit per one flower cluster" (which means the averaged number of the fruit bodies as formed in each single cluster of flowers).

The test results obtained are tabulated in Table 1 below.

TABLE 1

| Active Component Tested | Concentration of the active component compound in the agent sprayed (%) | Number of flower clusters tested | Number of flowers tested | Percentage of bearing cluster (%) | Percentage of fruit set (%) | Average number of fruit per flower cluster |
| --- | --- | --- | --- | --- | --- | --- |
| 2-Pyrrolidone-5- | 0.02 | 20 | 100 | 95 | 83 | 4.4 |
| Carboxylic Acid | 0.10 | 23 | 114 | 96 | 84 | 4.4 |
|  | 0.20 | 18 | 90 | 61 | 21 | 1.7 |
| Control (Not sprayed) | — | 41 | 205 | 98 | 53 | 2.7 |
| Sodium 2-Pyrroli- | 0.10 | 18 | 195 | 89 | 25 | 3.1 |
| done-5-Carboxylate | 0.20 | 20 | 159 | 75 | 18 | 1.9 |
| Control (Not sprayed) | — | 32 | 281 | 97 | 33 | 2.9 |
| N—Mixed Fatty | 0.02 | 20 | 100 | 100 | 75 | 3.8 |
| Acylated L-Gluta- | 0.10 | 21 | 104 | 100 | 61 | 3.0 |
| mic Acid Mono- | 0.20 | 18 | 90 | 61 | 21 | 1.7 |
| Sodium Salt | 0.50 | 22 | 110 | 64 | 20 | 1.6 |
| Control (Not sprayed) | — | 41 | 205 | 98 | 53 | 2.7 |

TABLE 1-continued

| Active Component Tested | Concentration of the active component compound in the agent sprayed (%) | Number of specimens tested | | Percentage of bearing cluster (%) | Percentage of fruit set (%) | Average number of fruit per flower cluster |
| --- | --- | --- | --- | --- | --- | --- |
| | | Number of flower clusters tested | Number of flowers tested | | | |
| Sucrose Mono- | 0.010 | 21 | 105 | 71 | 34 | 2.4 |
| Laurate | 0.050 | 21 | 105 | 67 | 31 | 2.3 |
| | 0.100 | 11 | 60 | 64 | 25 | 2.1 |
| | 0.400 | 18 | 150 | 44 | 15 | 0.3 |
| Control (Not sprayed) | — | 43 | 214 | 98 | 69 | 3.0 |
| Plant Sterols | 0.01 | 24 | 120 | 96 | 64 | 3.4 |
| | 0.05 | 18 | 90 | 100 | 60 | 3.0 |
| | 0.10 | 19 | 95 | 100 | 52 | 2.6 |
| Control (Not sprayed) | — | 22 | 110 | 100 | 78 | 3.9 |

EXAMPLE 6

Effect of the Time of Spraying of the Flower-thinning Agent on the Flower-thinning Effect of the Agent for Flower of Pear Tree According to the procedures of the foregoing Examples 1 and 3, the following three formulations were prepared:

an aqueous solution containing 0.2% of 2-pyrrolidone-5-carboxylic acid (abbreviated as PCA), an aqueous solution of containing 0.2% of sodium 2-pyrrolidone-5-carboxylate (referred to as PCA-Na), and an aqueous solution containing 0.5% of sucrose mono-laurate.

These three solutions were each sprayed onto the flowers of pear trees (variety: Hou-sui) on different times of application, and the effect of the time of spraying the solutions on the flower-thinning effects was estimated.

Thus, the aqueous solution containing the flower-thinning active compound was sprayed onto the flowers in different plots and at different and successive points of time where percentage of the number of the bloomed clusters of flower (which means the percentage of the number of the flower clusters of which any individual flower body had been bloomed out, as calculated on the basis of the total number of the flower clusters under test) were of different values as the time lapsed. For each plot of the flower so treated under test, the percentage of fruit set was evaluated in a similar way to the Example 5. The relationship between the percentage of fruit set and the different times of application of the flower-thinning agent (as expressed in term of the aforesaid "percentage of the number of the bloomed clusters of flower") were plotted in the graphs of FIGS. 1, 2 and 3 of the attached drawings. The axis of abscissa of the graphs represents the "percentage of the number of the bloomed clusters of flower", while the axis of ordinate of the graphs represents the percentage of fruit set as evaluated.

The test results obtained are shown in FIGS. 1 to 3. FIGS. 1, 2 and 3 show the results obtained with the solution of 0.2% PCA, with the solution of 0.2% PCA-Na, and with the solution of 0.5% sugar mono-laurate, respectively.

EXAMPLE 7

Flower Thinning on Peach Tree

According to the method as described in the Example 3, four, different aqueous solutions containing 0.001%, 0.01%, 0.05% or 0.1% of sucrose mono-laurate were prepared. These solutions were each sprayed onto the flowers of peach tree when 50% of the flowers had been bloomed out, and the flower-thinning effects were evaluated in a similar way to Example 5. The test results obtained is shown in Table 2 below.

TABLE 2

| Active component compound tested | Concentration of active component in the agent sprayed (%) | Number of flowers tested | Percentage of fruit set (%) |
| --- | --- | --- | --- |
| Sucrose mono-laurate | 0.001 | 80 | 43.8 |
| | 0.01 | 80 | 21.3 |
| | 0.05 | 74 | 20.3 |
| | 0.1 | 57 | 14.0 |
| No treatment | — | 553 | 50.8 |

EXAMPLE 8

Flower Thinning on Peach Tree

There were chosen 20 clusters of flower which were assumed to be bloomed out at the next day. In each cluster, 5 individual flower bodies were retained and all the other flower bodies were manually removed out of the flower cluster. The petals of the remaining flower bodies were manually opened, and the stamens of these flowers were manually removed out of each flower body.

Aqueous solutions containing 0.1%, 0.2% or 0.3% of the active component compound as indicated in Table 3 below were prepared according to the procedures of the Examples 2 and 3. These solutions were each sprayed onto the flowers as processed as above. These flowers so treated were subjected to artificial pollination at the next day. 6 Weeks later, the presence or absence of the fertilization was checked. For comparison purpose, some another flowers from which the stamens were similarly removed were sprayed merely with simple water and were then subjected to the similar artificial pollination at the next day.

The flower-thinning effects were evaluated in a similar way to the Example 5.

The test results obtained were shown in the Table 3 below.

TABLE 3

| Active component compound tested | Concentration of the active component compound in the agent tested (%) | Number of flower clusters tested | Number of flowers tested | Number of fruit set | Percentage of fruit set (%) |
| --- | --- | --- | --- | --- | --- |
| Control (Simple water) | — | 16 | 76 | 55 | 72.4 |
| N—mixed fatty acylated L-glutamic acid mono-sodium salt | 0.1 | 18 | 90 | 11 | 12.2 |
| | 0.2 | 18 | 89 | 34 | 38.2 |
| | 0.3 | 20 | 100 | 34 | 34.0 |
| Sucrose mono-laurate | 0.1 | 18 | 90 | 40 | 44.5 |
| | 0.2 | 20 | 100 | 42 | 42.0 |
| Sugar mono-stearate | 0.1 | 19 | 95 | 40 | 42.1 |
| | 0.2 | 17 | 85 | 40 | 47.1 |

EXAMPLE 9

Flower Thinning on Persimmon ("Kaki" in Japanese) Tree

Within one day after blooming of the flowers, flowers of 16-years-aged persimmon tree (variety: Sohsei-Jiro) were sprayed with different aqueous solutions of containing 0.01%, 0.05%, 0.1%, 0.2%, 0.5% or 1.0% of the active component compound as indicated in Table 4 below, by means of a hand sprayer. The flowers so treated were allowed to stand in the nature environment and not subjected to the artificial pollination. For comparison purpose, two plots of flowers which remained untreated with the flower-thinning agent were set on the same persimmon tree. The first of the untreated plots was subjected to the artificial fertilization, whereas the second of the untreated plots was prevented from the pollens entering thereinto. In the plot of such flowers which were prevented from receiving the pollens, the stigmas were cut off from the unbloomed flowers, so that spontaneous fertilization was inhibited in said plot. The flower-thinning effects of the above-mentioned treatment were estimated in a similar way to the Example 5. The test results obtained are shown in the Table 4.

TABLE 4

| Active compound tested | Concentration of the active compound in the agent tested (%) | Number of flowers tested | Percentage of fruit set (%) |
| --- | --- | --- | --- |
| 2-Pyrrolidone-5-carboxylic acid | 0.2 | 117 | 39.8 |
| 2-Pyrrolidone-5-carboxylic acid | 0.5 | 132 | 35.7 |
| 2-Pyrrolidone-5-carboxylic acid | 1.0 | 99 | 31.8 |
| Pollen prevented plot | — | 80 | 25.6 |
| Artificial pollination plot | — | 91 | 75.1 |
| N—mixed fatty acylated L-glutamic acid mono-sodium salt | 0.2 | 125 | 13.5 |
| N—mixed fatty acylated L-glutamic acid mono-sodium salt | 0.5 | 143 | 25.0 |
| N—mixed fatty acylated L-glutamic acid mono-sodium salt | 1.0 | 87 | 18.5 |
| Pollen prevented plot | — | 115 | 22.4 |
| Artificial pollination plot | — | 137 | 58.1 |
| Sucrose mono-laurate | 0.01 | 81 | 47.3 |
| Sucrose mono-laurate | 0.05 | 90 | 38.1 |
| Sucrose mono-laurate | 0.1 | 150 | 21.7 |
| Pollen prevented plot | — | 115 | 11.2 |
| Artificial pollination plot | — | 127 | 70.8 |

EXAMPLE 10

A 20 years-aged apple tree (variety: Fuji) was taken, and as the test specimens were chosen at random 10 clusters of flower which were carried by some fruit-harvesting short branches of the tree, these branches being positioned at the outer sides of the tree. At the time when 80~90% of the flowers in the flower clusters under test were bloomed, the flowers were treated by spraying with aqueous solutions containing the active component compounds at such concentrations as indicated in Table 5 below, by means of a hand sprayer. The sprayed aqueous solutions were containing a spreading agent in order to aid the sticking of the solution to the flowers. One day after the flower-thinning treatment with the sprayed aqueous solutions as above, the flowers so treated were subjected to artificial fertilization using the pollens of another apple tree (variety: Golder). One month after the treatment with the flower-thinning agent, the percentage of fruit set was evaluated on average in a similar way to the Example 5, separately for such flowers which were positioned at the center of each flower cluster, and for such flowers which are positioned at lateral or marginal places in each flower cluster. The total number of the bloomed flowers present in the whole clusters of flower under test was also counted separately for such flowers which were positioned at the center of each flower cluster and for such flowers which were positioned at the lateral or marginal places of each flower cluster, and "rate of cumulative blooming" was estimated in term of percentages of the total number of the bloomed "central" or "lateral" flowers, as calculated on the basis of the total number of the bloomed and unbloomed flowers present in the whole, ten clusters of flower under test. The test results obtained are tabulated in Table 5 below.

TABLE 5

| Active component compound tested | Concentration of the active component compound in the agent sprayed (%) | Number of flowers "central" flower | Number of flowers "lateral" flower | Cumulative blooming rate (%) "central" flower | Cumulative blooming rate (%) "lateral" flower | Percentage of fruit set (%) "central" flower | Percentage of fruit set (%) "lateral" flower |
| --- | --- | --- | --- | --- | --- | --- | --- |
| 2-pyrrolidone-5-carboxylic acid | 0.2 | 10 | 42 | 100 | 83 | 100 | 32.8 |
|  | 0.5 | 10 | 42 | 100 | 85 | 100 | 14.3 |
|  | 1.0 | 10 | 44 | 100 | 84 | 100 | 20.4 |
| N—mixed fatty acylated L-glutamic acid sodium salt | 0.2 | 10 | 47 | 100 | 87 | 100 | 56.8 |
|  | 0.5 | 10 | 41 | 100 | 81 | 100 | 56.1 |
|  | 1.0 | 10 | 44 | 100 | 80 | 100 | 56.8 |
| Sucrose monolaurate | 0.01 | 10 | 42 | 100 | 90 | 100 | 25.0 |
|  | 0.05 | 10 | 41 | 100 | 87 | 100 | 19.5 |
|  | 0.10 | 10 | 42 | 100 | 82 | 100 | 54.3 |
| Control (not sprayed) | — | 10 | 40 | 100 | 87 | 100 | 85.0 |

What we claim is:

1. A method for thinning flowers of cultivated fruit trees, which comprises applying to the flowers and/or to the body of a fruit tree an effective amount of at least one 2-pyrrolidone-5-carboxylic acid, a salt thereof, a salt of an N-higher aliphatic acylated glutamic acid, sucrose monolaurate, sucrose monostearate, and a mixture of plant sterols; said mixture of plant sterols comprising sitosterol, stigmasterol, campesterol, and brassicasterol.

2. A method according to claim 1 where said mixture of plant sterols is applied.

* * * * *

UNITED STATES PATENT AND TRADEMARK OFFICE
CERTIFICATE OF CORRECTION

PATENT NO. : 4,613,359
DATED : September 23, 1986
INVENTOR(S) : YAMAZAKI, ET AL.

It is certified that error appears in the above-identified patent and that said Letters Patent is hereby corrected as shown below:

Title page, item [73] should read as follows:

-- [73] Assignees: Director, Fruit Tree Research Station, Ministry of Agriculture, Forestry and Fisheries, Ibaragi, Japan; and Ajinomoto Co., Inc., Tokyo, Japan --

Signed and Sealed this

Twenty-sixth Day of October, 1993

Attest:

BRUCE LEHMAN

Attesting Officer

Commissioner of Patents and Trademarks